(12) United States Patent
Beaupré

(10) Patent No.: US 9,702,863 B2
(45) Date of Patent: Jul. 11, 2017

(54) METHOD AND PROBE FOR MEASURING BUOYANCY IN CONCRETE

(71) Applicant: I.B.B. RHÉOLOGIE INC., Quebec (CA)

(72) Inventor: Denis Beaupré, Sainte-Catherine-de-la-Jacques-Cartier (CA)

(73) Assignee: COMMAND ALKON DUTCH TECH B.V., Zoetermeer (NL)

( * ) Notice: Subject to any disclaimer, the term of this patent is extended or adjusted under 35 U.S.C. 154(b) by 126 days.

(21) Appl. No.: 14/775,373

(22) PCT Filed: Mar. 11, 2014

(86) PCT No.: PCT/CA2014/050210
§ 371 (c)(1),
(2) Date: Sep. 11, 2015

(87) PCT Pub. No.: WO2014/138968
PCT Pub. Date: Sep. 18, 2014

(65) Prior Publication Data
US 2016/0025700 A1   Jan. 28, 2016

Related U.S. Application Data

(60) Provisional application No. 61/781,542, filed on Mar. 14, 2013.

(51) Int. Cl.
*G01N 9/10* (2006.01)
*G01N 33/38* (2006.01)
(Continued)

(52) U.S. Cl.
CPC ......... *G01N 33/383* (2013.01); *B28C 5/422* (2013.01); *B28C 7/02* (2013.01); *G01N 9/08* (2013.01);
(Continued)

(58) Field of Classification Search
CPC .................................................. G01N 33/383
(Continued)

(56) References Cited

U.S. PATENT DOCUMENTS 2,630,706 A * 3/1953 Maxon, Jr. ............. G01N 11/10
200/52 R
4,981,042 A    1/1991 Reeves
(Continued)

FOREIGN PATENT DOCUMENTS

| EP | 0441770 A2 | 8/1991 |
| JP | 11023443 A | 1/1999 |
| RU | 2008650 C1 | 2/1994 |

OTHER PUBLICATIONS

"Rheological probe to measure Concrete Workability": Denis Beaupre 37th Conference on Our World in Concrete & Structures Aug. 29-31, 2012.
(Continued)

*Primary Examiner* — Walter L Lindsay, Jr.
*Assistant Examiner* — Philip Marcus T Fadul
(74) *Attorney, Agent, or Firm* — Norton Rose Fulbright Canada LLP; Alexandre Daoust

(57) ABSTRACT

The method can determine a density of concrete based on the measured buoyancy of a buoy immersed in fresh concrete contained in a ready mix drum and rotatable therein as the drum is rotated, the method can include obtaining a first measurement of a force applied to the buoy while the buoy is being moved tangentially in the fresh concrete, obtaining a second measurement of a force applied to the buoy while the buoy is being moved tangentially in the fresh concrete by rotation of the cylindrical wall, obtaining an indication of the buoyancy of the buoy in the concrete including factoring out the yield effect based on at least the first measurement and the second measurement.

21 Claims, 4 Drawing Sheets

(51) Int. Cl.
  *G01N 9/26* (2006.01)
  *G01N 9/14* (2006.01)
  *B28C 7/02* (2006.01)
  *B28C 5/42* (2006.01)
  *G01N 9/08* (2006.01)
  *G01N 9/36* (2006.01)
(52) U.S. Cl.
  CPC ................ *G01N 9/10* (2013.01); *G01N 9/14* (2013.01); *G01N 9/26* (2013.01); *G01N 9/36* (2013.01); *G01N 2009/263* (2013.01)
(58) Field of Classification Search
  USPC .......................................................... 73/433
  See application file for complete search history.

(56) References Cited

U.S. PATENT DOCUMENTS

| | | | |
|---|---|---|---|
| 6,227,039 B1 | 5/2001 | Te'eni | |
| 2012/0186341 A1* | 7/2012 | Oike | G01D 5/165 73/317 |
| 2015/0078417 A1* | 3/2015 | Verdino | G01K 1/024 374/142 |

OTHER PUBLICATIONS

"Measurement of Rheological Properties of High Performance Concrete: State of the Art report": Ferraris C.F. Journal of Research of the national Institute of Standard and Technology vol. 104, 1999, pp. 461-478.

* cited by examiner

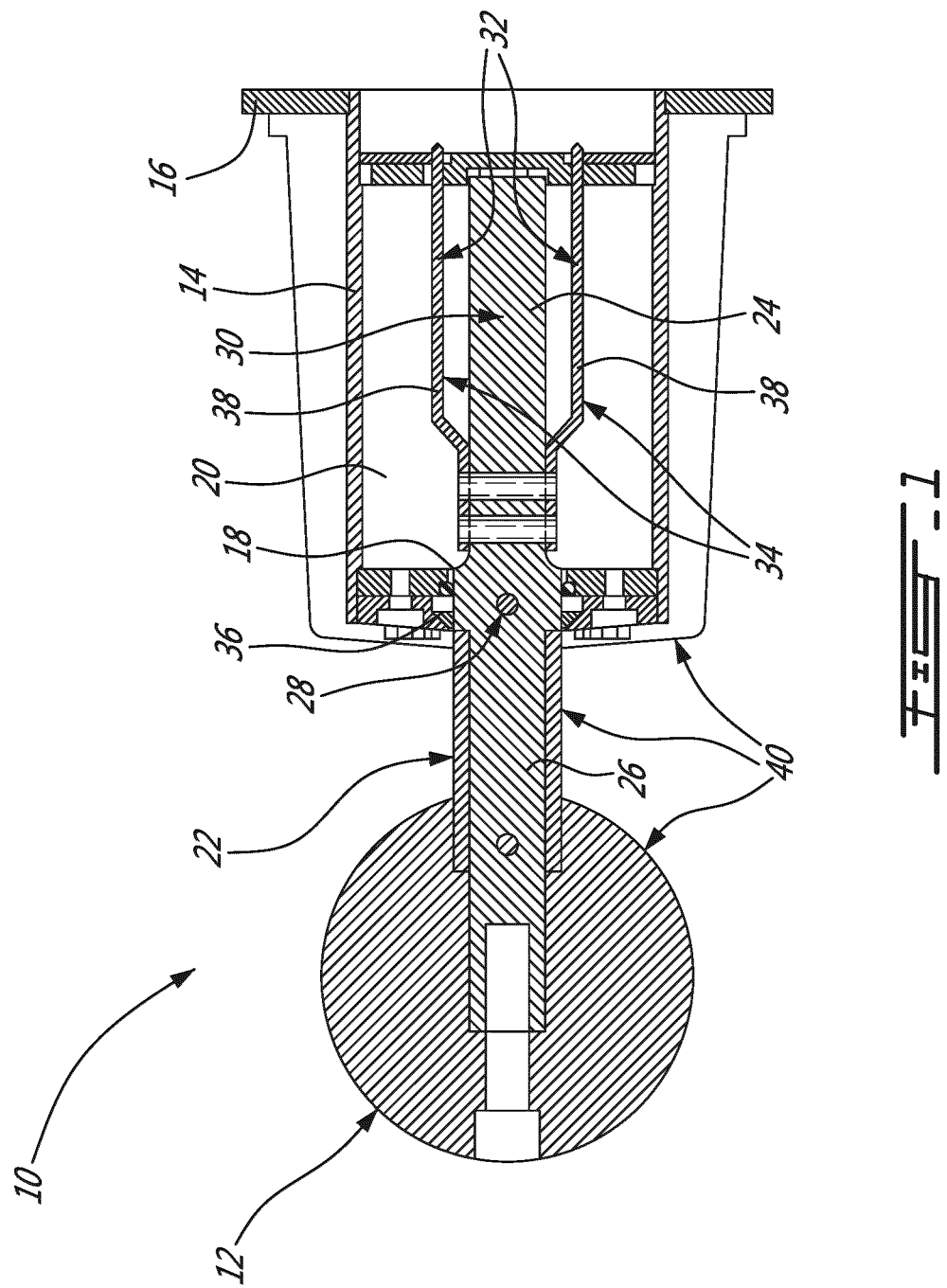

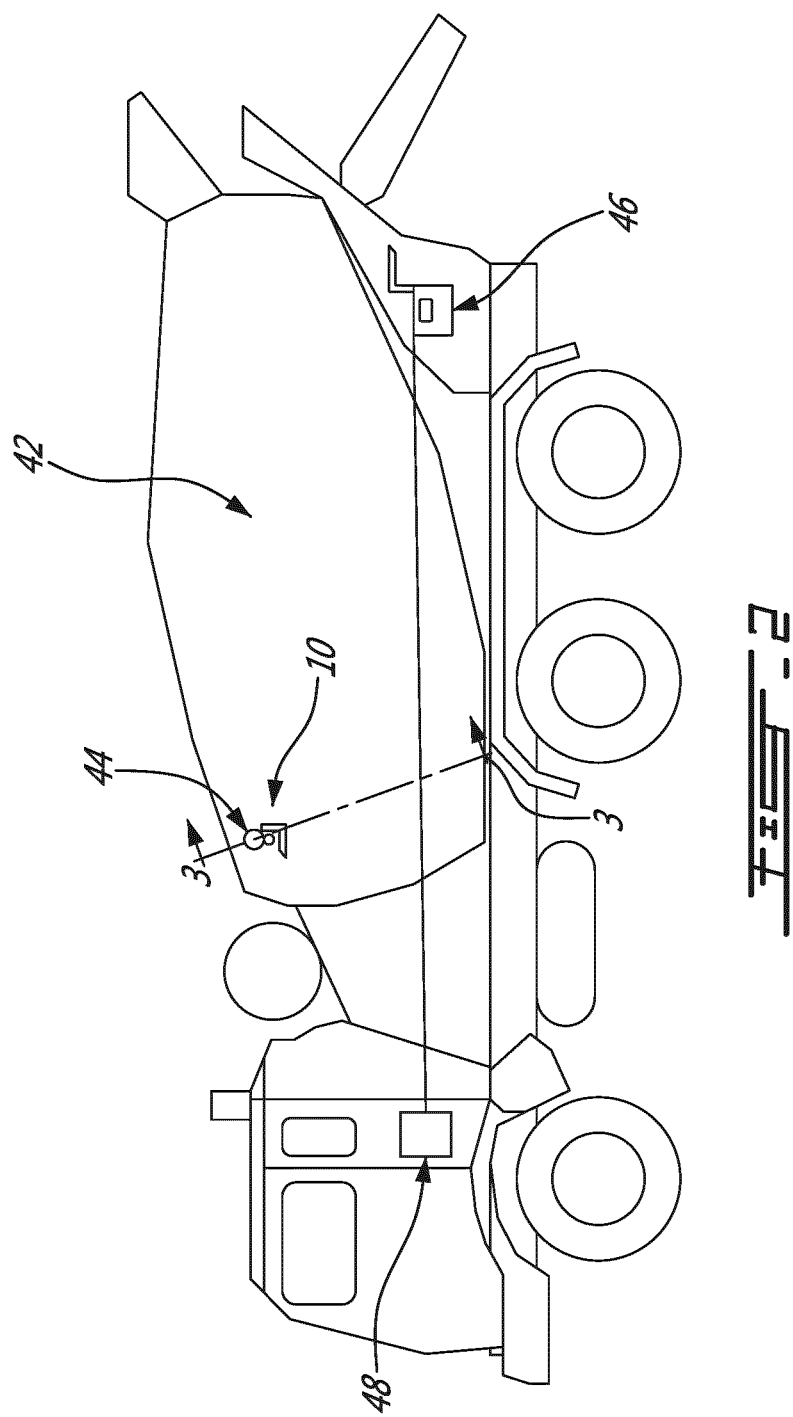

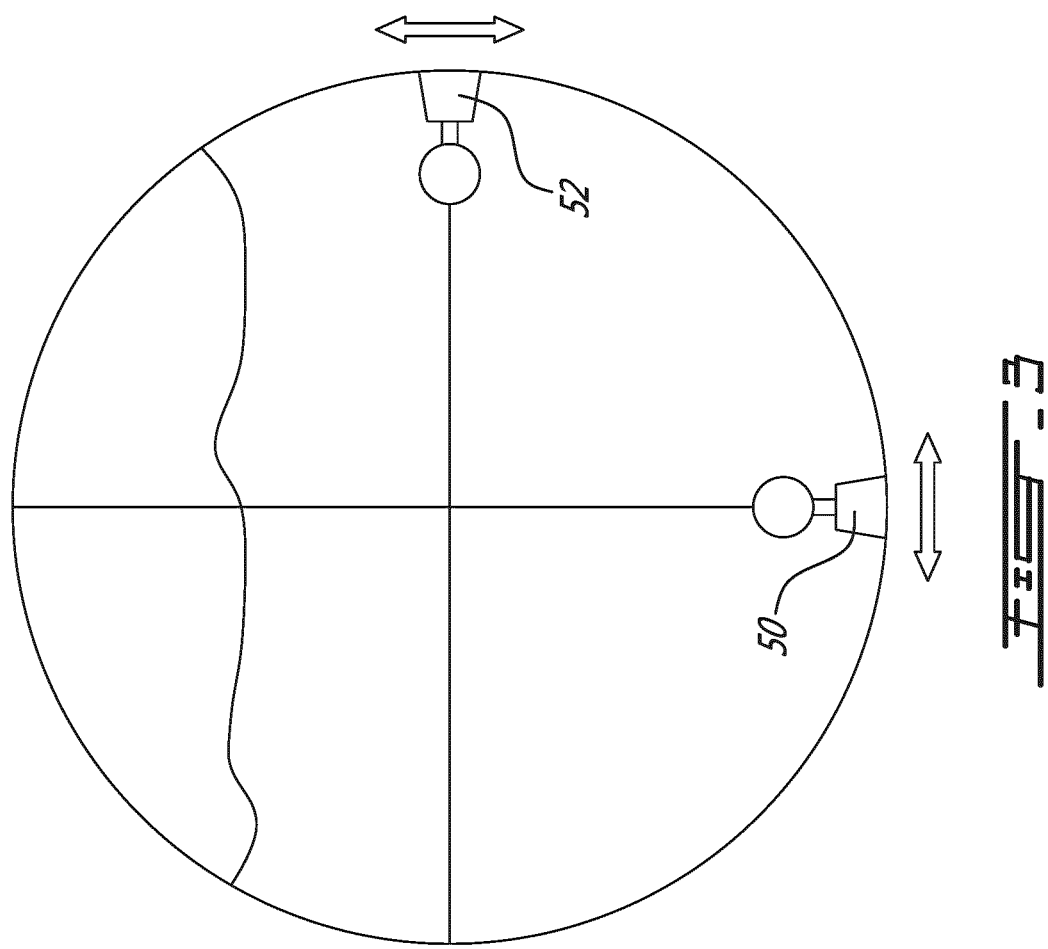

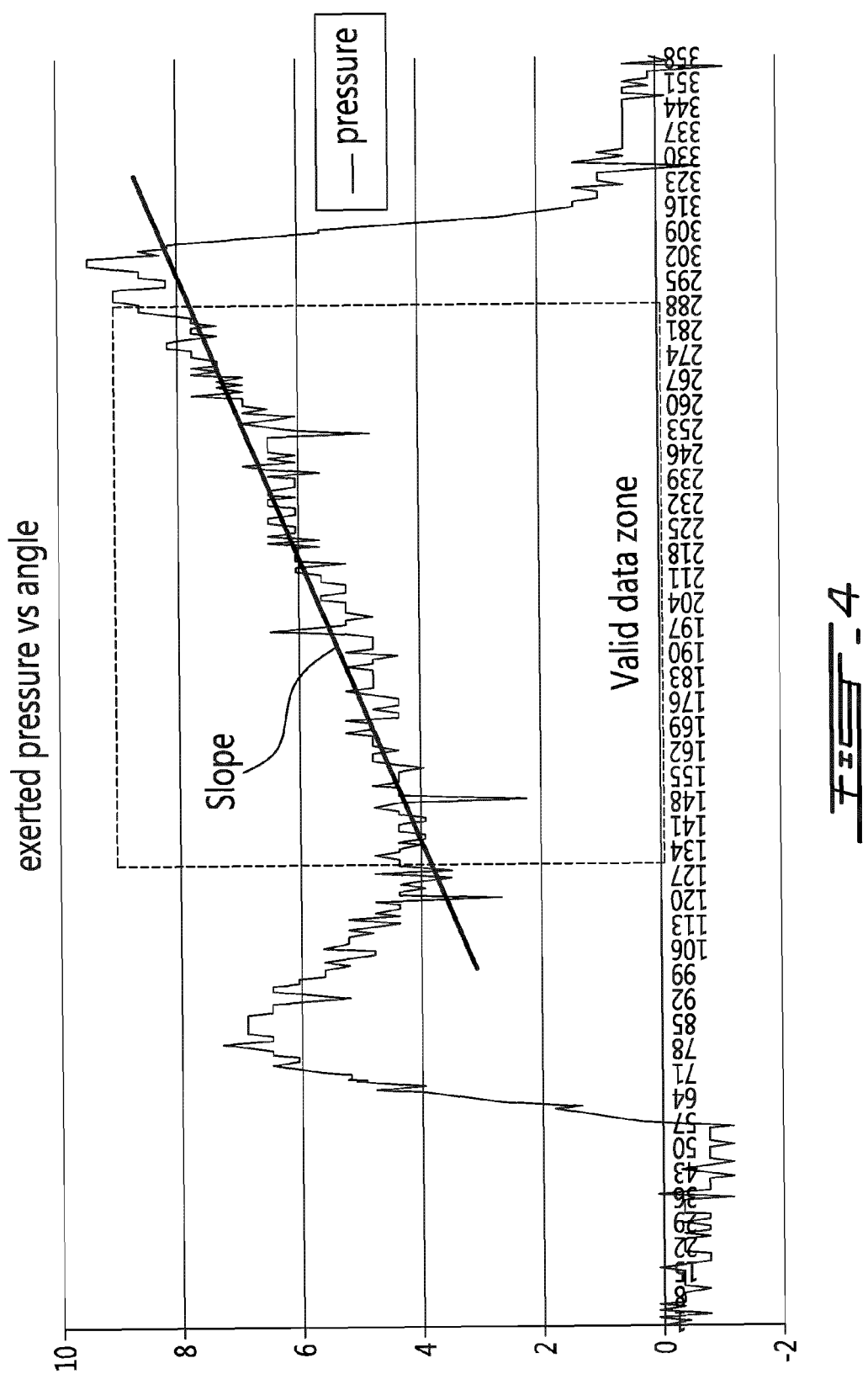

METHOD AND PROBE FOR MEASURING BUOYANCY IN CONCRETE

FIELD

The improvements generally relate to the field of concrete production, and more particularly refers to measuring buoyancy in concrete to allow evaluation of fresh concrete density and air content in ready mix drum.

BACKGROUND

It is well known in concrete industry that density of fresh concrete is affected by concrete composition and air content.

Density is usually calculated by dividing a known volume of material by its weight. For a given composition, the measured (including indirect method such as pressiometer) or calculated density of fresh concrete can be compared to the theoretical density without considering the presence of air to calculate the theoretical air content. The measure of density usually requires the use of a container of known volume that is filled with the fresh concrete and the weight of the concrete is determined by discounting the weight of the container.

Although the known methods to determine density were satisfactory to a certain degree, there remained room for improvement.

SUMMARY

A method of calculating buoyancy is provided which can be done without the need for sampling and moreover, automatically (without human intervention). The method can use a probe element immersed in fresh concrete in a ready mix drum. The calculated buoyancy can be used in determining the density of concrete, which, in turn, can be used in determining the air content.

In accordance with one aspect, there is provided a method of generating a signal indicative of buoyancy of a buoy immersed in fresh concrete contained in a ready mix drum rotatable about a central axis, the central axis being at least partially horizontally-oriented, said buoy being mounted on an inner surface of said drum and moved along a circular path when the drum is rotated, said method comprising: rotating the drum about the central axis, to move the buoy inside said fresh concrete across a vertical minimum position along the circular path, and measuring a first force exerted on said buoy as said buoy is moved across the vertical minimum position, said first force being representative of yield stress; rotating the drum about the central axis, to move the buoy inside said fresh concrete across a maximum lateral position along the circular path, and measuring a second force exerted on said buoy as said buoy is moved across the maximum lateral position, said second force being representative of combined yield stress and buoyancy; subtracting the measured first force across the vertical minimum position from the measured second force across the maximum lateral position; and generating a signal indicative of said buoyancy based at least on said subtraction.

In accordance with another aspect, there is provided a method of generating a signal indicative of a buoyancy of a buoy immersed in fresh concrete contained in a ready mix drum rotatable about a central axis, the central axis being at least partially horizontally-oriented, said buoy being mounted on an inner surface of said drum and moved along a circular path when the drum is rotated, said method comprising: obtaining a first measurement of a force applied to the buoy while the buoy is being moved tangentially in the fresh concrete by rotation of the cylindrical wall at a given speed, the first measurement including at least a yield effect of the buoy in the concrete; obtaining an indication of the position of the buoy along the circular path where the first measurement is obtained; obtaining a second measurement of a force applied to the buoy while the buoy is being moved tangentially in the fresh concrete by rotation of the cylindrical wall at the given speed, the second measurement including at least the yield effect and a buoyancy effect of the buoy in the concrete; obtaining an indication of the position of the buoy along the circular path where the second measurement is obtained; obtaining an indication of the buoyancy of the buoy in the concrete including factoring out the yield effect based on at least the first measurement, the indication of the position of the first measurement, the second measurement, and the indication of the position of the second measurement; generating a signal indicative of the buoyancy based on said obtained indication of the buoyancy.

In accordance with another aspect, there is provided a probe for use in fresh concrete in a ready mix drum rotatable about a central axis, the central axis being at least partially horizontally-oriented, said probe being mountable on an inner surface of said drum to be moved along a circular path when the drum is rotated, the probe comprising a housing having a base fixable to an interior surface of the cylindrical wall of the ready mix drum, the housing having an aperture opposite the base and enclosing an inner cavity between the aperture and the base; a pivoting member having a first end engaged in the inner cavity through the aperture and a second end protruding outwardly from the housing, away from the base, the pivoting member being pivotally mounted to the housing in a manner to be pivotable about a pivot axis positioned between the first end and the second end and oriented parallel to the central axis of the ready mix drum; a buoy made integral to the second end of the pivoting member and exhibiting a significant buoyancy in said fresh concrete, at least one deformable member mounted between the pivoting member and the housing, having a load cell mounted thereon to measure a pivoting force of the pivoting member around the pivot axis.

In accordance with another aspect, there is provided a method of determining density of a fluid in a drum rotatable about a central axis, the central axis being at least partially horizontally-oriented, based on pressure measurements obtained from a pressure sensor having given features and being mounted on an inner surface of the drum, as the pressure sensor is moved along a circular path associated to rotation of the drum at a constant speed relative to the fluid, the pressure measurements corresponding to the normal force exerted by the fluid against the surface of the pressure sensor as the pressure sensor is moved inside the fluid, the method comprising: obtaining a plurality of pressure measurements associated to corresponding angular positions of the pressure sensor in a valid data zone positioned between a minimum pressure position of the pressure sensor in the fluid and an area of entry or exit of the probe into or out from the fluid; determining a slope of the pressure measurements of the valid data zone; determining a density of the fluid based on the slope and known features of the pressure sensor.

In this specification, the expression buoy is used in a general manner to refer to a buoy which exhibits a significant positive or negative buoyancy in fresh concrete.

Many further features and combinations thereof concerning the present improvements will appear to those skilled in the art following a reading of the instant disclosure.

DESCRIPTION OF THE FIGURES

In the figures,

FIG. 1 is a view of an example of a probe which can be used to determine buoyancy of a buoy thereof immersed in fresh concrete;

FIG. 2 is a schematic view showing the probe of FIG. 1 mounted on an inner surface of a ready mix drum; and FIG. 3 is a schematic view, taken along cross-section lines 3-3 of FIG. 2, showing oscillating of the probe about a vertical minimum position and a lateral maximum position, both positions being disposed around a circular rotation path defined along the wall of the ready mix drum;

FIG. 4 is a graph showing normal pressure measurements plotted as a function of angular position of a pressure sensor as it is rotated in the rotary drum of a ready-mix truck.

DETAILED DESCRIPTION

Depending of the fluid properties and the density of a buoy, a buoy with positive buoyancy will raise (float) more or less rapidly, whereas a buoy with negative buoyancy will descend (sink) more or less rapidly. For a given buoy, the ascending or descending speed depends on the fluid viscosity, as described by Stoke's $2^{nd}$ law.

Fresh concrete is a complex material which exhibits a viscous characteristics but that also has, most of the time, a yield stress that must be overcome before any immersed buoy can start to move trough it (this explains why the aggregate material does not sink too much in fresh concrete). The shape of the immersed buoy, more precisely its projected surface in the direction of the movement, factored by the fluid yield stress, opposes the buoyancy force (in both directions when the buoy is not moving).

In theory, if one can measure or know the buoyancy forces on a buoy immerged in concrete, the volume of the buoy and the effect of the yield stress, it is possible to determine the density of the concrete. Accordingly, the following description explains an example of practical way to measure concrete yield stress inside the drum of the ready mix, and a way to determine the density of the concrete using this measurement.

As will be described in further detail below, in accordance with a first general method, measurements can be made at two particular positions within the circular travel path of a probe as the drum of the ready mix is rotated about its axis to isolate the buoyancy from the yield stress and factor the yield stress out of the equation.

More particularly, the position of the probe along the circular travel path can be determined using a position sensor which can optionally be combined into a probe having a load sensor. For reference, determination of position using a probe having accelerometers working in different axes is described in international patent publication no. WO 2011/042880.

FIG. 1 shows an example of a probe 10 which can incorporate a position sensor such as described in the above identified reference, for instance. Moreover, the example probe 10 shown in FIG. 1 is designed to harness the buoyancy of a buoy 12 immersed in fresh concrete. More specifically, the probe 10 includes a housing 14 having a base 16 fixable to an interior surface of the cylindrical wall of the ready mix drum, the housing 14 having an aperture 18 opposite the base 16 and enclosing an inner cavity 20 between the aperture 18 and the base 16. A pivoting member 22 is used, having a first end 24 engaged in the inner cavity 20 through the aperture 18 and a second end 26 protruding outwardly from the housing 14, away from the base 16, the pivoting member 22 being pivotally mounted to the housing 14 about a pivot axis 28 which is oriented parallel to the central axis of the ready mix drum when the probe 10 is mounted to the interior surface of the cylindrical wall of the ready mix drum (see FIG. 2). The pivoting member 22 is provided with the buoy 12 made integral to the second end 26, and a counterweight 30 provided by the first end 24. At least one deformable member 32, in this case two, are mounted between the pivoting member 22 and the housing 14 in a manner that load cells 34 mounted thereto can measure a rotary force exerted on the pivoting member 22 around the pivot axis 28. A load cell with protection for overload can be used in alternate embodiments.

The optional mechanical counterweight 30 is used in this embodiment to at least partially balance the weight of the buoy 12 about the axis 28 when the pivoting member 22 is oriented horizontally, thereby limiting the amount of pivoting force around the axis 28 which would imparted by the weight of the immersed buoy and the lever arm of the center of gravity with the pivot axis 28. A deformable soft seal 36 is used to bridge a gap associated with the aperture 18 which would otherwise be present between the pivoting member 22 and the housing 14, and thereby prevents concrete from entering the chamber 20, or inner cavity, where the load sensors 34 formed by the deformable members 32 and strain gages 38 glued thereon can measure the load. Protective and replaceable parts 40, such as protective jackets, can be used to shield components of the sensor, such as the housing 14, pivoting member 22, and immersion member 12, from abrasion from the concrete.

The seal 36 can be placed perpendicular to the normal flow of concrete (i.e. tangential to the rotation axis of the drum) to address wear.

The load sensor 34 is protected from overload by a rigid body (which, in this case, is provided in the form of a first end 24 of the pivoting member 22 engaged inside the cavity 20, and also serving as the counterweight 30). The rigid body restricts the movement of the immersed buoy. When the immersed buoy 12 is moved in the concrete, it tends to move around the pivoting axis 28 given the drag and yield stress exerted thereon by the concrete. This movement is restricted, to a certain extent, by the deformable members 32. When the deformation of the deformable member 32 (thus the load carried by the deformable member) reaches a certain value, the end part of the rigid body, which is free to move by some small angle, eventually comes into contact with an abutment that stops its movement, constraining it within a given angle span, and protecting the deformable members 32 from plastic deformation.

Although the shape and density of the buoy can significantly vary and still provide a workable solution, a sphere was selected in this embodiment. A sphere was found to provide a satisfactory volume/projected surface area ratio. It this case, the volume is increased to increase the buoyancy effect of the immersed buoy and the projected surface (the two dimensional projection of the body along the circular path) is kept satisfactorily low to reduce the effect of the concrete yield stress. Although a cube can provide an even better volume/projected surface area ratio, a sphere is still preferred because it results in less drag when moved in the concrete during normal operation of the ready mix drum and also does not have corners or edges. By comparison, the corners and edges of a cube would likely tend to wear rapidly, which would likely affect the projected surface area and/or the weight of the buoy and therefore affect the precision of the calculation of buoyancy according to the example method detailed below.

Similarly, the portion of the pivoting member 22 which extends between the deformable seal 36 and the buoy 12 is provided in a cylindrical shape in this embodiment, which similarly avoids undesired sharp edges.

In alternate embodiments, a buoy in the shape of a satisfactory hybrid between a sphere and a cube, and a protruding portion of the pivoting member in the shape of a satisfactory hybrid between a rectangular prism and a cylinder can be used, for instance. In still another alternate embodiment, the buoy can be provided in the form of a hollow cylindrical second end of the pivoting member having a rounded tip, for instance.

Referring to FIG. 2, the probe 10 can be mounted inside the drum of a ready mix truck 42. The load detected by the load sensors can be sent to a processing unit 44 by wireless communication device to a receiver 46 that can be connected to a long range communication device 48 such as used by cellular phone technology, for instance.

In according with one example method, as shown in FIG. 3, the drum is moved to position the probe at two determined positions referred to herein as the vertical minimum position 50 and lateral, or horizontal, maximum position 52.

During one of these steps, the drum is moved at constant low speed and for small angles back and forth across the vertical minimum position, during which time the pivoting force exerted on the pivoting member is measured (using the load cells in this example). In this vertical position, the effects of buoyancy on the pivoting force are negligible since the buoyancy force is exerted radially relative to the pivot axis and therefore does not contribute to pivot the pivoting member about the pivot axis. In other words, the buoyancy force is not detected by the load cells in this example when the probe is at the vertical minimum position. The measured load is thus indicative of yield stress on the immersed buoy (without having to use two different speeds).

The speed at which the measures are taken should be low, such as lower than 0.1 rotation per minute for instance, for a typical ready mix drum of a concrete truck. The lower and more constant the speed is, the higher the precision of the measure will likely be. However, lower speed will typically also lead to a longer time period to conduct the measures and the calculations. In the illustrated embodiment, especially considering that yield can change as a function of time, it was preferred to complete the entire buoyancy calculation within a maximum of 5 minutes, and preferably about 2 minutes. For instance, speed can be between 0.01 and 0.05 RPM and the small angle movement can be performed for angles within 5 degrees of the original vertical position (e.g. between 1-2 degrees) in order not to bias the yield stress measurement with buoyancy effects.

To increase precision, it is recommended to make several oscillations around the vertical position and to record the average load measured in both clockwise and counterclockwise directions. If it is desired to measure not only yield stress, but also viscosity, measurements at two different speeds can be made such as described in international patent publication WO 2011/042880. If only yield stress measurement is sought, the measurement made at low speed has been demonstrated to allow evaluating the yield stress with sufficient precision to provide a valid determination of density using the method described herein.

During another step, the same measurement of the pivoting force on the pivoting member is done while the probe is moved around the horizontal position 16. The movements can be the same as those described above in terms of speed and angle limits. In the horizontal position, buoyancy affects the pivoting force, in addition to the effects of yield stress. With the yield stress being obtained from the oscillation around the vertical position, the portion of the pivoting force relating to buoyancy can be obtained simply by subtracting yield stress imparted load from the total measured load.

A servo control hydraulic valve can be used to automatically place the sensor at the desired position and proceed with the small movements indicated in the procedure described above. Type 4WSE3E 25 directional servo-valve in 4-way version, manufactured by Bosch Rexroth AG, is an example of a servo control hydraulic valve which can be used to this end, for instance. This process can be performed when the level of the concrete above the sensor in the horizontal position is high enough to not affect the measurement of the load (i.e. to maintain the probe fully immersed).

With the volume of the buoy known (from its geometry), and the distance between its center of gravity and the pivot axis also know, the buoyancy force is determined and the density of the concrete (or other fluid) can be calculated in a manner exemplified below where measured loads were converted into pressures, considering the lever arm of each force, for convenience and ease of calculation:

P1: Equivalent pressure on immersed buoy measured in clockwise direction in minimal vertical (bottom) position.

P2: Equivalent pressure on immersed buoy measured in anti-clockwise direction in minimal vertical (bottom) position.

P3: Equivalent pressure on immersed buoy measured in clockwise direction in horizontal (mid-level) position.

P4: Equivalent pressure on immersed buoy measured in anti-clockwise direction in horizontal (mid-level) position.

In theory, P1 should equal P2, and neglecting the effect of gravity or weight, the buoyancy pressure "$B_{press}$" can be calculated in the following ways (where a positive value is obtained in the case where the buoy exhibits positive buoyancy for instance):

$$B_{press} = P3 - (P1 \text{ or } P2) \quad (1)$$

or $$B_{press} = P4 + (P1 \text{ or } P2) \quad (2)$$

or $$B_{press} = (P3 - P4)/2 \quad (3)$$

In this embodiment, it was preferred to take an average calculation or to calculate with the following equation:

$$B_{press} = (P3 - P4 + P2 - P1)/2 \quad (4)$$

Which also allows to factor out many undesirable practical effects such as those which can be associated to uneven response of the load cells in the clockwise and the counter-clockwise directions or those associated to imperfect counterbalancing of the weight of the buoy 1 by the counterweight 2, such as detailed below.

For example, If P1=0.2 kPa, P2=0.3 kPa, P3=0.6 kPa and P4=1.1 kPa, then the buoyancy pressure (over the total projected surface of the immersed buoy) equal 0.9 kPa or 900 N/m2.

If the total projected surface area (Area) of the sphere and short connection arm is 6000 mm$^2$ and the total volume (Vol)

is 300,000 mm³, or 0.3 liters) then the buoyancy forces "$B_{force}$" of the fluid can be calculated by:

$$`B_{force}` = B_{press} \times Area \qquad (5)$$

which provides '$B_{force}$'=900 N/m2×0.006 m2=5.4 N in this case, which is also equal to the "equivalent" mass multiplied by the gravitational acceleration (g=9.82 m/s²). The "equivalent mass" is thus 5.4/9.81=0.55 kg.

In some embodiments, where replaceable wear parts are in contact with concrete, the probe can be provided with a model of their wear rate (change in shape, volume, weight, etc. over a given period of use), in which case the effect of their wear can be considered in the calculation. A protective jacket 40 can be used to protect the seal 36, as shown in FIG. 1.

The density "D" of the fluid is equal to "equivalent mass" divided by the volume divided by the density of water (approx 1 kg/liter). The density "D" is thus (0.55 kg/0.3 liter)/1 kg/liter=1.8

For the above density of 1.8, if the apparent density (AD) of the concrete (density without considering the presence of air content) is 2.4, then the air content can be calculated as follows:

$$Air(percent) = (1 - D/AD) \times 100 \qquad (6)$$

For the above example, the air content would be: Air=(1−(1.8/2.4))×100=25%.

It will be noted that in the example provided above, the forces are measured in both clockwise and anti-clockwise directions. In fact, theoretically, P1 is equal to P2, since both represent only Yield at the vertical minimum position. However, as illustrated in the example provided above, even when based on a plurality of averaged values, P1 is not equal to P2. This is caused by practical effects which can occur within the sensor, such as friction for instance, which causes the sensor, or more particularly the load cells, to behave slightly, though significantly, differently in the two different directions. These undesired practical effects within the sensor are overcome in the example method provided above by using the measures in both the clockwise and the counter-clockwise directions in equation (4) in order to provide an 'average value' which was found more representative of the actual value in cases where these undesirable practical effects occur.

Should such 'unevenness' be absent in alternate embodiments, i.e. where the P1 measurement would always be operatively equal to the P2 measurement and the undesired practical effects would be negligible, the buoyancy can be obtained from equation (3) above, and only the two associated measurements can be taken. This can be interesting because the two measurements P3 and P4 associated to equation (3) are made at the same position (the horizontal maximum position in this case) which can allow obtaining the buoyancy indication more rapidly than by using equation (4), for instance.

Moreover, still in alternate applications where the undesired practical effects referred to above are considered negligible, determining the buoyancy can be even simpler if the probe is provided with a counterweight which entirely counterbalances (within workable tolerances) the pivotal force caused by the weight of the buoy 1 around the pivot when the immersion buoy is in the lateral maximum position. In other words, P3 or P4 can be said to include $$P3 = Yield\ stress_{effect} + B_{press} - W_{effect} \qquad (7)$$

$$P4 = Yield\ stress_{effect} - B_{press} + W_{effect} \qquad (8)$$

It can be understood that in such a case, any undesired weight effect (e.g. weight of the pivoting member and associated components exerting a significant moment of force in any direction around the pivot when in the horizontal maximum position, see below) are factored out using equation (3) or (4) above, but can bias the use of equation (1) or (2).

In the embodiment of the probe 10 illustrated in FIG. 1, the buoy 12, together with the entire portion of the pivoting member 22 extending past the pivot 28 when in the horizontal orientation, has a weight which has the effect of a downwardly oriented force acting on a center of gravity offset from the pivot 28 by a lever arm distance, and therefore imparts a moment around the pivot 28. The counterweight 30 together with the entire portion of the pivoting member 22 extending on the opposite side of the pivot 28 relative the buoy 12, also has the effect of a downwardly oriented force acting on a corresponding other center of gravity, also offset from the pivot 28 but on the other side. Henceforth, in the horizontal position, the counterweight 30 exerts a moment around the pivot 28 which counteracts the moment associated to the buoy 12. $W_{effect}$ can be said to be the effect of the net balance between these two counteracting moments, where a negative value was selected to indicate a weight-imparted moment of force opposite the one associated to the buoyancy in this example.

Should the probe be engineered for the counterweight to precisely counteract the weight associated to the buoy, $W_{effect}$ can be considered negligible, i.e. ~0. In such a case, it will be understood that a satisfactory indication of buoyancy can also be obtained by either one equations (1) or (2) above, rather than having to factor out this effect using equations (3) or (4), for instance.

In practice, it can be difficult to adjust the effect of the counterweight to a satisfactory degree of precision. For instance, the buoy 12 can wear off over time, and its weight be affected. Moreover, the load cells 34 in this embodiment are mounted on deformable members 32 which can also cause a weight effect which can be complicated to factor in. These inconveniences were satisfactorily overcome in this embodiment by taking the measures in both directions, at both the vertical and lateral positions, and using equation (4).

It will be understood that the example detailed above uses the horizontal position and also uses the vertical minimum position to within a satisfactory degree of precision (e.g. within 5 degrees). The advantage of using these positions has been outlined above and can be summarized by saying that in the vertical minimum position, the tangential component of buoyancy (the only component which can be measured using the probe 10 shown in FIG. 1), is nil, which allows to single out the effect of Yield stress; whereas in the horizontal maximum position, the effect of buoyancy is entirely tangential, which directly allows to measure its full effect.

It will be understood that in alternate embodiments, still using a probe which measures only forces in the tangential orientation such as described above, but using slightly more complicated mathematics, satisfactory results can be obtained by taking measures at other positions than those described above. For instance, if a measure is taken at, say, 45 degrees from the vertical minimum position, it can be understood that the detected forces associated to yield and buoyancy are proportionally reduced from the corresponding actual forces in a manner which can be determined using relatively simply trigonometric calculations. In this manner, back and forth movements at the 45° position referred to above can allow to factor out yield and determine buoyancy using equation (3) and the associated trigonometric factor, assuming that weight and unevenness undesired practical effects are negligible.

This can be advantageous because it allows using a sensor 10 such as shown in FIG. 2, which only calculates the tangential component of the buoyancy force (the radial component of the buoyancy force being fully absorbed by the pivoting member, and more precisely its pivot in the illustrated example). Alternately, still using a sensor similar to the one detailed above and illustrated, but assuming that weight effects and/or unevenness undesired effects are present, a satisfactory buoyancy indication can still be obtained by taking measurements of the tangential forces in both clockwise and anti-clockwise directions at two different, and known, positions of the immersed probe along the circular path. This can result in a set of two equations having two unknowns for which mathematical resolution will allow to isolate both the yield and buoyancy force.

In still alternate embodiments, an indication of the buoyancy can be obtained by taking measures at a single position by using a sensor which measure tangential forces such as described above, but which can additionally measure radial buoyancy forces. For instance, tangential force measures can be taken when the probe is moved in the tangential direction during one step, and an other step can include measuring the radial buoyancy force at the same position while the drum is not rotated. The position can conveniently be selected to be the vertical minimum position, for instance, in which the buoyancy force is exerted fully in the radial direction, which allows to readily determine the Yield from the tangential force measurement and then subtract it from the radial force measurement. The radial force measurement can be obtained using a buoy exhibiting positive or negative buoyancy. The radial force measurement can include freeing the buoy to allow radial movement over a short distance (e.g. 1 mm), and measuring the residual force at the end of this short distance (e.g. using a traction load cell), for instance. A mechanism, e.g. electromagnetic, can be provided to selectively hold or release buoy to this end. Assuming a positive buoyancy, for instance, a buoy entraining buoyancy forces that are greater than the yield forces is required, which can require selecting an appropriate volume/projected surface ratio for the immersed body in accordance with the explanations provided above, for instance.

The expression buoy is used liberally in the context of this specification as it will be understood that a probe such as is described in international patent publication no. WO 2011/042880, though difficultly associable to a buoy in the everyday use of the term, can present sufficient buoyancy to act as a buoy in the sense intended in this specification.

A second general method of determining density is now presented with reference to FIG. 4.

When there is a certain minimum level of fluid concrete in the drum of the ready-mix truck, the concrete is homogeneous, and the relative speed between the concrete and the sensor is constant in the vicinity of the sensor throughout the measurements, the density of the fluid can be determined from force pressures using a pressure/force measurement probe (a potential example of which is described in international patent publication no. WO 2011/042880). This can be advantageous in some embodiments.

A way to achieve this involves recording the exerted pressure on the sensor and the associated sensor angle at a plurality of positions along the path of the sensor in the fluid. The relationship between pressure and angle depends on the sensor shape and volume as well as of the density of the fluid in which the sensor is traveling. That relationship is expected to be non-linear. An example of such a record is plotted in the graph presented in FIG. 4 which shows a sudden increase in pressure and a sudden decrease in pressure associated with the entry and exit of the probe into and out from the concrete, respectively.

A first step is to extract a set of data which will be referred to herein as the valid data set, associated with a valid data zone of the graph, from the overall data. The valid data zone can be determined to be associated with the portion of the graph where the pressure sensor is in the concrete, and more specifically to begin at a minimum pressure point in the concrete and be terminated before the position of exit of the pressure sensor from the concrete. In this example embodiment, the valid data zone is more specifically determined to finish a little before the point of exit to a sufficient extent to avoid pressure perturbations which can be expected to occur around the point of exit of the pressure sensor. The extent of the valid data zone depends on the level of concrete in the drum.

A second step is to plot or otherwise calculate a linear relationship curve which is best fitted with the valid data set. This best-fit linear relationship curve is proportional to the concrete density in accordance with a coefficient which is a factor of the fluid and the geometrical and mechanical features of the pressure sensor. Henceforth, the proportionality coefficient can be calibrated against measurements of slope for fluids of known density. This technique can be extended to fluids other than concrete being mixed in rotary containers equipped with suitable normal-force pressure sensors (i.e. pressure sensors adapted to determine the normal force imparted against the pressure sensor by the fluid as the pressure sensor is moved in the fluid).

As can be seen therefore, the examples described above and illustrated are intended to be exemplary only. The scope is indicated by the appended claims.

What is claimed is:

1. A method of generating a signal indicative of buoyancy of a buoy immersed in fresh concrete contained in a ready mix drum rotatable about a central axis, the central axis being at least partially horizontally-oriented, said buoy being mounted on an inner surface of said drum and moved along a circular path when the drum is rotated, said method comprising:
    rotating the drum about the central axis, to move the buoy inside said fresh concrete across a vertical minimum position along the circular path, and measuring a first force exerted on said buoy as said buoy is moved across the vertical minimum position, said first force being representative of yield stress;
    rotating the drum about the central axis, to move the buoy inside said fresh concrete across a maximum lateral position along the circular path, and measuring a second force exerted on said buoy as said buoy is moved across the maximum lateral position, said second force being representative of combined yield stress and buoyancy;
    subtracting the measured first force across the vertical minimum position from the measured second force across the maximum lateral position; and
    generating a signal indicative of said buoyancy based at least on said subtraction.

2. The method of claim 1 wherein said moving across a vertical minimum position and said moving across a lateral maximum position both include effecting a back and forth movement at the corresponding position, and both the measuring the first force and the measuring the second force includes averaging a plurality of measures taken at a given speed in the corresponding same direction.

3. The method of claim 2 wherein a third force is measured at the same position than the first force, by averaging a plurality of measures taken in the corresponding opposite direction, and a fourth force is measured at the same position than the second force, by averaging a plurality of measures taken at a given speed in the corresponding opposite direction.

4. The method of claim 3 further comprising subtracting the measured second force from the measured fourth force, adding the results of both subtractions, dividing the result of the addition by two, and said generating a signal is based on the result of the division.

5. The method of claim 1 further comprising calculating density of said fresh concrete using a known volume of said immersed buoy and said signal.

6. The method of claim 5 further comprising comparing said calculated density to a theoretical density to determine air content.

7. A probe for use in fresh concrete in a ready mix drum rotatable about a central axis, the central axis being at least partially horizontally-oriented, said probe being mountable on an inner surface of said drum to be moved along a circular path when the drum is rotated, the probe comprising
a housing having a base fixable to an interior surface of the cylindrical wall of the ready mix drum, the housing having an aperture opposite the base and enclosing an inner cavity between the aperture and the base;
a pivoting member having a first end engaged in the inner cavity through the aperture and a second end protruding outwardly from the housing, away from the base, the pivoting member being pivotally mounted to the housing in a manner to be pivotable about a pivot axis positioned between the first end and the second end and oriented parallel to the central axis of the ready mix drum;
a buoy made integral to the second end of the pivoting member and exhibiting a significant buoyancy in said fresh concrete,
at least one deformable member mounted between the pivoting member and the housing, having a load cell mounted thereon to measure a pivoting force of the pivoting member around the pivot axis.

8. The probe of claim 7 wherein the second end of the pivoting member acts as a counterweight to the buoy such that a pivoting effect stemming from the weight of the second end of the pivoting member cancels an opposite pivoting effect stemming from the weight of a first end of the pivoting member and of the immersion buoy made integral thereto when the probe is immersed in the fresh concrete and held at a horizontal maximum position along the circular path.

9. The probe of claim 7 wherein a deformable seal extends between the pivoting member and the housing, closing the aperture, the deformable seal extending generally tangentially relative to the central axis.

10. The probe of claim 7 wherein the buoy is spherical.

11. The probe of claim 10 wherein a portion of the second end extending between the deformable seal and the buoy is cylindrical.

12. The probe of claim 7 further comprising a replaceable protection jacket covering at least one of the housing, the pivoting member, and the immersion buoy for shielding from said concrete in said ready mix drum.

13. The probe of claim 7 further comprising a counterweight to the buoy, said counterweight being made integral to the first end.

14. The probe of claim 13 wherein the counterweight has a weight comparable to the weight of the buoy.

15. The method of claim 7 wherein the ready mix drum is rotated at a relatively constant speed of less than 0.1 RPM during said measurements.

16. The method of claim 7 wherein the ready mix drum is rotated at a relatively constant speed of less than 0.1 RPM during said measurements.

17. A method of determining density of a fluid in a drum rotatable about a central axis, the central axis being at least partially horizontally-oriented, based on pressure measurements obtained from a pressure sensor having given features and being mounted on an inner surface of the drum, as the pressure sensor is moved along a circular path associated to rotation of the drum at a constant speed relative to the fluid, the pressure measurements corresponding to the normal force exerted by the fluid against the surface of the pressure sensor as the pressure sensor is moved inside the fluid, the method comprising:
Obtaining a plurality of pressure measurements associated to corresponding angular positions of the pressure sensor in a valid data zone positioned between a minimum pressure position of the pressure sensor in the fluid and an area of entry or exit of the probe into or out from the fluid;
Determining a slope of the pressure measurements of the valid data zone;
Determining a density of the fluid based on the slope and known features of the pressure sensor.

18. The method of claim 17 wherein the fluid is concrete and the drum is the drum of a ready-mix truck.

19. The method of claim 17 wherein the valid data zone is positioned between the minimum pressure position and an area of exit of the probe.

20. The method of claim 17 wherein the area of entry or exit of the probe corresponds to an area of perturbations associated with the entry or exit of the probe from the fluid.

21. The method of claim 17 wherein the obtaining further comprises obtaining pressure sensor measurements corresponding to a en entire period of immersion of the pressure sensor in the fluid and determining the valid data zone based on a minimum pressure measurement of the pressure sensor in the fluid and a maximum pressure measurement of the pressure sensor.

* * * * *